(12) United States Patent
Jensen et al.

(10) Patent No.: US 6,797,694 B2
(45) Date of Patent: Sep. 28, 2004

(54) CHEMICAL COMPOUNDS HAVING ION CHANNEL BLOCKING ACTIVITY FOR THE TREATMENT OF IMMUNE DYSFUNCTION

(75) Inventors: Bo Skaaning Jensen, Kobenhavn (DK); Soren Peter Olsen, Klampenborg (DK); Palle Christophersen, Ballerup (DK)

(73) Assignee: Poseidon Pharmaceuticals A/S, Ballerup (DK)

( * ) Notice: Subject to any disclaimer, the term of this patent is extended or adjusted under 35 U.S.C. 154(b) by 0 days.

(21) Appl. No.: 09/986,725

(22) Filed: Nov. 9, 2001

(65) Prior Publication Data

US 2002/0065247 A1 May 30, 2002

Related U.S. Application Data

(63) Continuation-in-part of application No. PCT/DK00/00253, filed on May 12, 2000.

(30) Foreign Application Priority Data

May 12, 1999 (DK) .......................................... 1999 00659

(51) Int. Cl.[7] ........................ A61K 31/065; A61K 31/44
(52) U.S. Cl. ........................ 514/11; 514/257; 514/277; 514/317; 514/357; 514/365; 514/374; 514/400; 514/427; 514/438; 514/461; 514/471; 514/544; 514/570; 514/617; 514/679; 514/717; 514/726
(58) Field of Search ........................ 514/315, 726–679, 514/736, 732, 11, 257, 277, 317, 357, 365, 374, 400, 427, 438, 461, 471, 544, 570, 617, 717, 492

(56) References Cited

U.S. PATENT DOCUMENTS

| | | | |
|---|---|---|---|
| 4,996,193 A | 2/1991 | Hewitt et al. | 514/11 |
| 5,512,591 A | 4/1996 | Halperin et al. | 514/399 |
| 5,540,931 A | 7/1996 | Hewitt et al. | 424/434 |
| 5,591,763 A | 1/1997 | Halperin et al. | 514/399 |
| 5,643,936 A | 7/1997 | Halperin et al. | 514/399 |
| 6,028,103 A | 2/2000 | Brugnara et al. | 514/492 |

FOREIGN PATENT DOCUMENTS

| | | |
|---|---|---|
| WO | WO 9418967 A1 | 9/1994 |
| WO | WO 9601107 A1 | 1/1996 |
| WO | WO 9734589 A1 | 9/1997 |
| WO | WO 9925347 A2 | 5/1999 |

OTHER PUBLICATIONS

Verheugen et al., *Cell Calcium*, vol. 21, No. 1, pp. 1–17 (1997).

Rader et al., *The Journal of Immunology*, vol. 156, pp. 1425–1430 (1996).

*Primary Examiner*—Richard L. Raymond
(74) *Attorney, Agent, or Firm*—Birch, Stewart, Kolasch & Birch, LLP

(57) ABSTRACT

The present invention relates to chemical compounds having inhibitory activity on an intermediate conductance $Ca^{2+}$ activated potassium channel ($IK_{Ca}$), and the use of such compounds for the treatment or alleviation of diseases or conditions relating to immune dysfunction.

6 Claims, 1 Drawing Sheet

CHEMICAL COMPOUNDS HAVING ION CHANNEL BLOCKING ACTIVITY FOR THE TREATMENT OF IMMUNE DYSFUNCTION

This application is a Continuation-In-Part of PCT International Application No. PCT/DK00/00253 filed on May 12, 2000, which was published in English and which designated the United States and on which priority is claimed under 35 U.S.C. § 120, the entire contents of which are hereby incorporated by reference.

TECHNICAL FIELD

The present invention relates to chemical compounds having inhibitory activity on an intermediate conductance $Ca^{2+}$ activated potassium channel ($IK_{Ca}$), and the use of such compounds for the treatment or alleviation of diseases or conditions relating to immune dysfunction.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

Many drugs exert their effects via modulation of ion channels. Examples are anti-epileptic compounds like Phenytoin and Lamotrigine, which block voltage dependent $Na^+$-channels in the brain, anti-hypertensive drugs like Nifedipine and Diltiazem, which block voltage dependent $Ca^{2+}$-channels in smooth muscle cells, and stimulators of insulin release like Glibenclamide and Tolbutamide, which block an ATP-regulated $K^+$-channel in the pancreas.

There is a large and still growing demand for non-toxic immune-regulating agents for use in relation to e.g. organ transplantation and auto-immune diseases.

Some of the currently used immune-suppressive compounds such as Cyclosporin A and FK506 prevent immunological proliferation by inhibition of the $Ca^{2+}$/calmodulin-dependent Ser/Thr phosphatase calcineurin. The usefulness of this class of compounds is limited by their side effects such as renal dysfunction, arterial hypertension, neurological effects (headache, insomnia, tremors, parasthesias, lethargy), gastrointestinal effects (nausea, vomiting, diarrhoea), and diabetes.

Another class of compounds comprising e.g. Azathioprine and Mizorbine interfere in a cytotoxic manner directly with the DNA-replication process. Although cytotoxicity shows some selectivity towards strongly proliferating cells such as activated T- and B-lymphocytes, complications may follow due to effects on dividing cells in the entire body, including bone marrow, hair sacs, the skin, testis, ovary and epithelia such as the airways, the intestinal tract, and the thick ascending limp of the loop of Henle's.

A fairly new approach for suppression of immune responses is to interfere with ion channels in the plasma membrane of cells in the immune system, especially the T- and B-lymphocytes. Upon exposure to antigens by antigen presenting macrophages or to mitogens such as IL-2 or IFN-γ, an initial signal in the switching from the resting phase to the proliferating phase is an activation of the phosphoinositide signalling pathway resulting in an increase in the intracellular concentration of $Ca^{2+}$ ($[Ca^{2+}]_i$) due to $Ca^{2+}$ release from intracellular stores. A sustained elevated $[Ca^{2+}]_i$ is maintained by an increased passive influx through mitogen regulated, voltage-independent Ca-channels. This increase in $[Ca^{2+}]_i$, is vital for the subsequent events leading to cell proliferation and secretion of lymphokines.

In resting T- and B-lymphocytes, the $[Ca^{2+}]$ is approximately $10^7$ fold higher outside versus inside the cell, and the membrane potential is negative inside, i.e. there is an inwardly directed electrochemical $Ca^{2+}$ gradient. Thus, when the Ca-channels are activated they conduct Ca into the cell. However, $Ca^{2+}$ influx via the Ca-channels, tends to reduce or even eliminate this gradient, and thus to reduce the influx. Concomitant opening of K-channels keeps the membrane potential negative, and activation of these channels is therefore essential for maintaining a large inwardly directed, electrochemical driving force for $Ca^{2+}$.

In the presence of blockers of lymphocyte K-channels, the cells depolarise, and thereby the $Ca^{2+}$ influx necessary for the activation of the immune response is reduced.

Several types of K-channels have been described in B- and T-lymphocytes including both voltage-dependent K-channels ($K_v$), and voltage-independent $Ca^{2+}$-activated K-channels ($K_{Ca}$). It is well established, that the $K_v$-channels are activated by the $Ca^{2+}$-induced depolarisation of the lymphocyte, and non-selective blockers of $K_v$-channels are therefore quite effective immune-suppressive agents. However, these compounds in general have severe side effects due to block of re polarization in excitable tissue (seizures, myotonic runs, high blood pressure, etc.).

Considerable effort has been made into the development of immune-selective $K_v$-blockers. The molecular rationale for this, has been the observation that T-lymphocytes express homomeric $K_v1.3$-channels in contrast to excitable cells, which always express several heteromeric subtypes of the $K_v$-channels.

A selective blocker of the $K_v1.3$-homomer might therefore be an ideal, relatively non-toxic, immune-suppressive agent. Initial reports from these pharmacological programs indicate that selective $K_v1.3$-blockers are very effective as anti-inflammatory agents. However, the well-known toxicity of non-selective $K_v$-blockers has apparently not disappeared. An example is the potent $K_v1.3$ blocker CP-339,818. This compound is also a potent blocker of $K_v1.4$, a cardiac and neuronal A-type K-channel. The side-effect of this compound is predicted to be interference with the cardiac action potential (long QT-syndrome toxicity) as well as with the action potential repolarization and after hyperpolarization in neurons.

WO 97/34589 describes triaryl methane compounds that inhibit mammalian cell proliferation, inhibit the Gardos channel of erythrocytes, reduce sickle erythrocyte dehydration and/or delay the occurrence of erythrocyte sickling or deformation, and suggest the use of these compounds in abnormal cell proliferation. However, the effect of these compounds on human T cell proliferation, the use of such compounds in normal cell proliferation as immune-suppressive agents, as well as their unexpected properties when used in combination therapy has never been disclosed.

SUMMARY OF THE INVENTION

A hitherto untested alternative to the block of the voltage-dependent K-channels is a selective inhibition of the $Ca^{2+}$-activated K-channels in T- and B-lymphocytes. These channels are directly activated by the increased $[Ca^{2+}]_i$ which is the primary signal for lymphocyte activation. Further, contrary to $K_v$-channels, these channels are voltage-independent, and therefore they do not close upon hyperpolarization, implicating that they are even more effective than $K_v$ channels in maintaining a large inward driving force on $Ca^{2+}$ under conditions of elevated intercellular $Ca^{2+}$-concentrations.

Two types of $Ca^{2+}$-activated K-channels have been described from lymphocytes: 1) Small-conductance, apamin-sensitive, $Ca^{2+}$-activated K-channels ($SK_{Ca}$) and 2) Intermediate-conductance, inwardly rectifying, Clotrimazole-sensitive, $Ca^{2+}$-activated K-channels ($IK_{Ca}$), also referred to as Gardos-channels. Resting T-lymphocytes express both $SK_{Ca}$ and $IK_{Ca}$, whereas B-lymphocytes only express $IK_{Ca}$.

Upon activation, prior to cell proliferation, the expression level of $IK_{Ca}$ increases approximately 30 fold in both T- and B-lymphocytes. The expression levels of both $K_v1.3$ and $SK_{Ca}$ remain unchanged, indicating a major role for the $IK_{Ca}$-channel in induction of T- and B-cell proliferation. Contrary to the $SK_{Ca}$-channels, which are extensively expressed in CNS and heart (measured as mRNA abundance by Northern hybridisation) and in PNS, skeletal muscle, hepatocytes (measured as functional channels by electrophysiology), expression of $IK_{Ca}$-channels have never been reported from any excitable tissue. In fact, blood cells such as erythrocytes, monocytes, lymphocytes, endothelial cells, and certain cell-lines with an epithelial ancestry, Ehrlich ascites tumour cells and HeLa cells appear to be the main source of this type of channels.

Furthermore, the very recent cloning of $IK_{Ca}$ has enabled the demonstration of the mRNA for this gene in several organs including placenta, salivary glands, lung and pancreas. Thus, specific blockers of $IK_{Ca}$ are likely to be very effective as immune-suppressive agents, and devoid of side effects on excitable tissue. In fact, the $IK_{Ca}$-inhibitor Clotrimazole (which is also a blocker of the cytochrome P-450 system) has been extensively used clinically in the systemic treatment of fungal infections. No toxicity related to K-channel blockade has been described.

Accordingly, in its first aspect, the invention relates to the use of a chemical compound having $IK_{Ca}$ inhibitory activity for the manufacture of a medicament for the treatment or alleviation of diseases, disorders or conditions relating to immune dysfunction.

In another aspect the invention provides a pharmaceutical compositions for use in the treatment or alleviation of diseases, disorders or conditions relating to immune dysfunction, comprising an effective amount of a chemical compound having $IK_{Ca}$ inhibitory activity.

DETAILED DISCLOSURE OF THE INVENTION

The present invention relates to the use of a chemical compound having selective $IK_{Ca}$ inhibitory activity for treatment or alleviation of diseases or conditions relating to immune dysfunction.

Chemical Compound Having $IK_{Ca}$ Inhibitory Activity

According to the invention, chemical compounds having selective $IK_{Ca}$ inhibitory activity may be identified by its ability to inhibit current through an $IK_{Ca}$ channel, while showing essentially no effect at other potassium channels at a 10 fold higher concentration, as determined by conventional patch clamp technique.

The compounds for use according to the invention show $IK_{Ca}$ inhibitory activity in concentrations below 100 μM, preferably below 10 μM, more preferred below 1 μm. In its most preferred embodiment compounds show $IK_{Ca}$ inhibitory activity show activity in low micromolar and the nanomolar range.

In a preferred embodiment the chemical compounds for use according to the invention showing selective $IK_{Ca}$ inhibitory activity are triaryl methane derivatives represented by the general Formula I

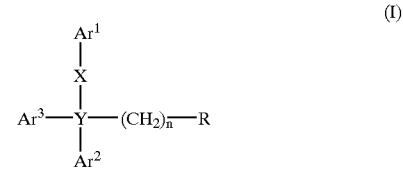

and a pharmaceutically acceptable salt or an oxide or a hydrate thereof, wherein, n is 0, 1, 2, 3, 4, 5 or 6;

X is absent, or represent a group of the formula —(CH$_2$)$_n$—, of the formula —(CH$_2$)$_n$—Z— (in either direction), of the formula —(CH$_2$)$_n$—CH=N— (in either direction), the formula —(CH$_2$)$_n$—Z—(CH$_2$)$_m$—, or of the formula —(CH$_2$)$_n$—CH=N—(CH$_2$)$_m$— (in either direction), or a group of the formula —R'''C(O)N—;

in which formulas n and m, independently of each another, represent 0, 1, 2, 3 or 4; and Z represents O, S, or NR''', wherein R''' represents hydrogen or alkyl;

Y represents a carbon atom (C), a nitrogen atom (N), or a phosphor atom (P), a silicium atom (Si), or a germanium atom (Ge);

Ar$^1$, Ar$^2$ and Ar$^3$, independently of each another, represents a partially or completely saturated mono- or polycyclic aryl group, or a mono- or poly-heterocyclic group, which mono- or polycyclic groups may optionally be substituted one or more times with substituents selected from the group consisting of halogen, trihalogenmethyl, alkyl, cycloalkyl, alkenyl, alkynyl, amino, nitro or cyano, or a group of the formula —OR'', —SR'', —R'OR'', —R'SR'', —C(O)R'', —C(S)R'', —C(O)OR'', —C(S)OR'', —C(O)SR'', —C(S)SR'', —C(O)NR'(OR''), —C(S)NR'(OR''), —C(O)NR' (SR''), —C(S)NR'(SR''), —CH(CN)$_2$, —C(O)NR''$_2$, —C(S)NR''$_2$, —CH[C(O)R'']$_2$, —CH[C(S)R'']$_2$, —CH [C(O)OR'']$_2$, —CH[C(S)OR'']$_2$, —CH[C(O)SR'']$_2$, —CH[C(S)SR'']$_2$, —CH$_2$OR'', or —CH$_2$SR'';

R represents hydrogen, halogen, trihalogenmethyl, alkyl, cycloalkyl, alkenyl, alkynyl, amino, nitro or cyano, or a group of the formula —OR', —SR', —R''OR', —R''SR', —C(O)R', —C(S)R', —C(O)OR', —C(S) OR', —C(O)SR', —C(S)SR', —C(O)NR''(OR'), —C(S)NR''(OR'), —C(O)NR''(SR'), —C(S)NR''(SR'), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, —CH$_2$OR', or —CH$_2$SR'; or a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR', or —SR'; and R' and R'', independently of each another, represents hydrogen, alkyl, cycloalkyl, alkenyl, alkynyl, or alkoxy.

In a more preferred embodiment, the triaryl methane derivative for use according to the invention is represented by the general Formula I wherein;

the partially or completely saturated mono- or polycyclic aryl group is selected from the group consisting phenyl, biphenyl, naphthyl, or cyclopenta-2,4-diene-1-ylidene; and the mono- or poly-heterocyclic group is A 5- and 6 membered heterocyclic monocyclic group selected from the group consisting of furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, piperidyl, pyrazinyl, pyrazolyl, pyridazinyl, pyridyl, pyrimidinyl, pyrrolidinyl, pyrrolyl, thiadiazolyl, thiazolyl, thienyl, and butyrolactonyl, in particular γ-butyrolactonyl.

In another preferred embodiment the triaryl methane derivative for use according to the invention is represented by the general Formula II

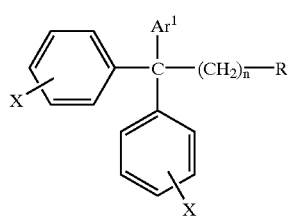

(II)

and a pharmaceutically acceptable salt or an oxide or a hydrate thereof, wherein, n is 0, 1, 2, 3, 4, 5 or 6;

$Ar^1$ represents a partially or completely saturated mono- or polycyclic aryl group, or a mono- or poly-heterocyclic group, which mono- or polycyclic groups may optionally be substituted one or more times with substituents selected from the group consisting of halogen, trihalogenmethyl, alkyl, cycloalkyl, alkenyl, alkynyl, amino, nitro or cyano, or a group of the formula —OR", —SR", —R'OR", —R'SR", —C(O)R", —C(S)R", —C(O)OR", —C(S)OR", —C(O)SR", —C(S)SR", —C(O)NR'(OR"), —C(S)NR'(OR"), —C(O)NR'(SR"), —C(S)NR'(SR"), —CH(CN)$_2$, —C(O)NR"$_2$, —C(S)NR"$_2$, —CH[C(O)R"]$_2$, —CH[C(S)R"]$_2$, —CH[C(O)OR"]$_2$, —CH[C(S)OR"]$_2$, —CH[C(O)SR"]$_2$, —CH[C(S)SR"]$_2$, —CH$_2$OR", or —CH$_2$SR";

R represents hydrogen, halogen, trihalogenmethyl, alkyl, cycloalkyl, alkenyl, alkynyl, amino, nitro or cyano, or a group of the formula —OR', —SR', —R"OR', —R"SR', —C(O)R', —C(S)R', —C(O)OR', —C(S)OR', —C(O)SR', —C(S)SR', —C(O)NR"(OR'), —C(S)NR"(OR'), —C(O)NR"(SR'), —C(S)NR"(SR'), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, —CH$_2$OR', or —CH$_2$SR'; or a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR', or —SR';

which triaryl methane derivative may further be substituted one or more times with a substituent X selected from the group consisting of hydrogen, halogen, trihalogenmethyl, alkyl, cycloalkyl, alkenyl, alkynyl, amino, nitro or cyano, or a group of the formula —OR", —SR", —R'OR", —R'SR", —C(O)R", —C(S)R", —C(O)OR", —C(S)OR", —C(O)SR", —C(S)SR", —C(O)NR'(OR"), —C(S)NR'(OR"), —C(O)NR'(SR"), —C(S)NR'(SR"), —CH(CN)$_2$, —C(O)NR"$_2$, —C(S)NR"$_2$, —CH[C(O)R"]$_2$, —CH[C(S)R"]$_2$, —CH[C(O)OR"]$_2$, —CH[C(S)OR"]$_2$, —CH[C(O)SR"]$_2$, —CH[C(S)SR"]$_2$, —CH$_2$OR", or —CH$_2$SR"; and R' and R", independently of each another, represents hydrogen, alkyl, cycloalkyl, alkenyl, alkynyl, or alkoxy.

In a more preferred embodiment, the triaryl methane derivative for use according to the invention is represented by the general Formula II wherein;

the partially or completely saturated mono- or polycyclic aryl group is selected from the group consisting phenyl, biphenyl, naphthyl, or cyclopenta-2,4-diene-1-ylidene; and the mono- or poly-heterocyclic group is A 5- and 6 membered heterocyclic monocyclic group selected from the group consisting of furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, piperidyl, pyrazinyl, pyrazolyl, pyridazinyl, pyridyl, pyrimidinyl, pyrrolidinyl, pyrrolyl, thiadiazolyl, thiazolyl, thienyl, and butyrolactonyl, in particular γ-butyrolactonyl.

In a third preferred embodiment the triaryl methane derivative for use according to the invention is represented by the general Formula III

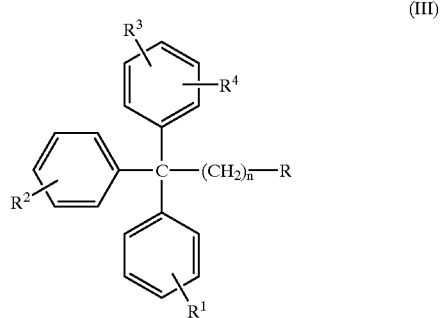

(III)

and a pharmaceutically acceptable salt or an oxide or a hydrate thereof, wherein, n is 0, 1, 2, 3, 4, 5, or 6;

R represents hydrogen, halogen, trihalogenmethyl, alkyl, cycloalkyl, alkenyl, alkynyl, amino, nitro or cyano, or a group of the formula —OR', —SR', —R"OR', —R"SR', —C(O)R', —C(S)R', —C(O)OR', —C(S)OR', —C(O)SR', —C(S)SR', —C(O)NR"(OR'), —C(S)NR"(OR'), —C(O)NR"(SR'), —C(S)NR"(SR'), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, —CH$_2$OR', or —CH$_2$SR'; or a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR', or —SR';

$R^1$, $R^2$, $R^3$ and $R^4$, independently of each another, represents hydrogen, halogen, trihalogenmethyl, alkyl, cycloalkyl, alkenyl, alkynyl, amino, nitro or cyano, or a group of the formula —OR", —SR", —R'OR", —R'SR", —C(O)R", —C(S)R", —C(O)OR", —C(S)OR", —C(O)SR", —C(S)SR", —C(O)NR'(OR"), —C(S)NR'(OR"), —C(O)NR'(SR"), —C(S)NR'(SR"), —CH(CN)$_2$, —C(O)NR"$_2$, —C(S)NR"$_2$, —CH[C(O)R"]$_2$, —CH[C(S)R"]$_2$, —CH[C(O)OR"]$_2$, —CH[C(S)OR"]$_2$, —CH[C(O)SR"]$_2$, —CH[C(S)SR"]$_2$, —CH$_2$OR", or —CH$_2$SR"; and R' and R", independently of each another, represents hydrogen, alkyl, cycloalkyl, alkenyl, alkynyl, or alkoxy.

In a more preferred embodiment, the triaryl methane derivative for use according to the invention is represented by the general Formula III wherein the partially or completely saturated mono- or polycyclic aryl group is selected from the group consisting phenyl, biphenyl, naphthyl, or cyclopenta-2,4-diene-1-ylidene; and the mono- or poly-heterocyclic group is A 5- and 6 membered heterocyclic monocyclic group selected from the group consisting of furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, piperidyl, pyrazinyl, pyrazolyl, pyridazinyl, pyridyl, pyrimidinyl, pyrrolidinyl, pyrrolyl, thiadiazolyl, thiazolyl, thienyl, and butyrolactonyl, in particular γ-butyrolactonyl.

In a fourth preferred embodiment the triaryl methane derivative for use according to the invention is represented by the general Formula IV

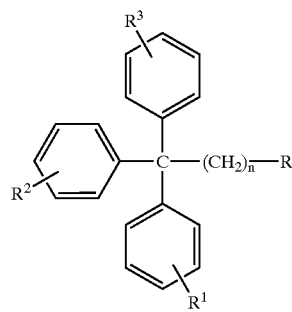

(IV)

and a pharmaceutically acceptable salt or an oxide or a hydrate thereof, wherein, n is 0, 1, 2, 3, 4, 5, or 6;

R represents hydrogen, halogen, trihalogenmethyl, alkyl, cycloalkyl, alkenyl, alkynyl, amino, nitro or cyano, or a group of the formula —OR', —SR', —R"OR', —R"SR', —C(O)R', —C(S)R', —C(O)OR', —C(S)OR', —C(O)SR', —C(S)SR', —C(O)NR"(OR'), —C(S)NR"(OR'), —C(O)NR"(SR'), —C(S)NR"(SR'), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, —CH$_2$OR', or —CH$_2$SR'; or a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR', or —SR';

$R^1$, $R^2$ and $R^3$, independently of each another, represents hydrogen, halogen, trihalogenmethyl, alkyl, cycloalkyl, alkenyl, alkynyl, amino, nitro or cyano, or a group of the formula —OR", —SR", —R'OR", —R'SR", —C(O)R", —C(S)R", —C(O)OR", —C(S)OR", —C(O)SR", —C(S)SR", —C(O)NR'(OR"), —C(S)NR'(OR"), —C(O)NR'(SR"), —C(S)NR'(SR"), —CH(CN)$_2$, —C(O)NR"$_2$, —C(S)NR"$_2$, —CH[C(O)R"]$_2$, —CH[C(S)R"]$_2$, —CH[C(O)OR"]$_2$, —CH[C(S)OR"]$_2$, —CH[C(O)SR"]$_2$, —CH[C(S)SR"]$_2$, —CH$_2$OR", or —CH$_2$SR"; and R' and R", independently of each another, represents hydrogen, alkyl, cycloalkyl, alkenyl, alkynyl, or alkoxy.

In a more preferred embodiment, the triaryl methane derivative for use according to the invention is represented by the general Formula IV wherein the partially or completely saturated mono- or polycyclic aryl group is selected from the group consisting phenyl, biphenyl, naphthyl, or cyclopenta-2,4-diene-1-ylidene; and the mono- or poly-heterocyclic group is A 5- and 6 membered heterocyclic monocyclic group selected from the group consisting of furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, piperidyl, pyrazinyl, pyrazolyl, pyridazinyl, pyridyl, pyrimidinyl, pyrrolidinyl, pyrrolyl, thiadiazolyl, thiazolyl, thienyl, and butyrolactonyl, in particular γ-butyrolactonyl.

In a fifth preferred embodiment the triaryl methane derivative for use according to the invention is represented by the general Formula V (V)

and a pharmaceutically acceptable salt or an oxide or a hydrate thereof, wherein, n is 0, 1, 2, 3, 4, 5, or 6;

$Ar^1$ represents a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR", —SR", —R'OR", —R'SR", —C(O)R", —C(S)R", —C(O)OR", —C(S)OR", —C(O)SR", —C(S)SR", —C(O)NR'(OR"), —C(S)NR'(OR"), —C(O)NR'(SR"), —C(S)NR'(SR"), —CH(CN)$_2$, —C(O)NR"$_2$, —C(S)NR"$_2$, —CH[C(O)R"]$_2$, —CH[C(S)R"]$_2$, —CH[C(O)OR"]$_2$, —CH[C(S)OR"]$_2$, —CH[C(O)SR"]$_2$, —CH[C(S)SR"]$_2$, —CH$_2$OR", or —CH$_2$SR";

R represents hydrogen, halogen, trihalogenmethyl, alkyl, cycloalkyl, alkenyl, alkynyl, amino, nitro or cyano, or a group of the formula —OR', —SR', —R"OR', —R"SR', —C(O)R', —C(S)R', —C(O)OR', —C(S)OR', —C(O)SR', —C(S)SR', —C(O)NR"(OR'), —C(S)NR"(OR'), —C(O)NR"(SR'), —C(S)NR"(SR'), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, —CH$_2$OR', or —CH$_2$SR'; or a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR', or —SR';

$R^1$ and $R^2$, independently of each another, represents hydrogen, halogen, trihalogenmethyl, alkyl, cycloalkyl, alkenyl, alkynyl, amino, nitro or cyano, or a group of the formula —OR", —SR", —R'OR", —R'SR", —C(O)R", —C(S)R", —C(O)OR", —C(S)OR", —C(O)SR", —C(S)SR", —C(O)NR'(OR"), —C(S)NR'(OR"), —C(O)NR'(SR"), —C(S)NR'(SR"), —CH(CN)$_2$, —C(O)NR"$_2$, —C(S)NR"$_2$, —CH[C(O)R"]$_2$, —CH[C(S)R"]$_2$, —CH[C(O)OR"]$_2$, —CH[C(S)OR"]$_2$, —CH[C(O)SR"]$_2$, —CH[C(S)SR"]$_2$, —CH$_2$OR", or —CH$_2$SR"; and R' and R", independently of each another, represents hydrogen, alkyl, cycloalkyl, alkenyl, alkynyl, or alkoxy.

In a more preferred embodiment, the triaryl methane derivative for use according to the invention is represented by the general Formula V wherein;

the partially or completely saturated mono- or polycyclic aryl group is selected from the group consisting phenyl, biphenyl, naphthyl, or cyclopenta-2,4-diene-1-ylidene; and the mono- or poly-heterocyclic group is A 5- and 6 membered heterocyclic monocyclic group selected from the group consisting of furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, piperidyl, pyrazinyl, pyrazolyl, pyridazinyl, pyridyl, pyrimidinyl, pyrrolidinyl, pyrrolyl, thiadiazolyl, thiazolyl, thienyl, and butyrolactonyl, in particular γ-butyrolactonyl.

In a sixth preferred embodiment the triaryl methane derivative for use according to the invention is represented by the general Formula VI

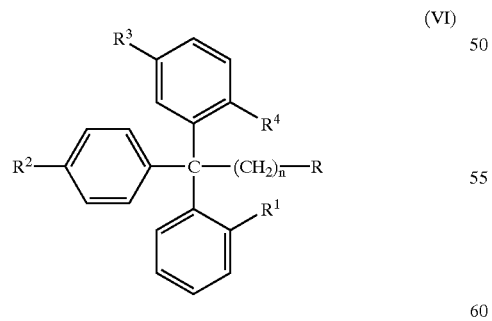

(VI)

and a pharmaceutically acceptable salt or an oxide or a hydrate thereof,
wherein,
n is 0, 1, 2, 3, 4, 5, or 6;
R represents hydrogen, halogen, trihalogenmethyl, alkyl, cycloalkyl, alkenyl, alkynyl, amino, nitro or cyano, or a group of the formula —OR', —SR', —R"OR', —R"SR', —C(O)R', —C(S)R', —C(O)OR', —C(S)OR', —C(O)SR', —C(S)SR', —C(O)NR"(OR'), —C(S)NR"(OR'), —C(O)NR"(SR'), —C(S)NR"(SR'), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, —CH$_2$OR', or —CH$_2$SR'; or a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR', or —SR';

$R^1$, $R^2$, $R^3$ and $R^4$, independently of each another, represents hydrogen, halogen, trihalogenmethyl, alkyl, cycloalkyl, alkenyl, alkynyl, amino, nitro or cyano, or a group of the formula —OR", —SR", —R'OR", —R'SR", —C(O)R", —C(S)R", —C(O)OR", —C(S)OR", —C(O)SR", —C(S)SR", —C(O)NR'(OR"), —C(S)NR'(OR"), —C(O)NR'(SR"), —C(S)NR'(SR"), —CH(CN)$_2$, —C(O)NR"$_2$, —C(S)NR"$_2$, —CH[C(O)R"]$_2$, —CH[C(S)R"]$_2$, —CH[C(O)OR"]$_2$, —CH[C(S)OR"]$_2$, —CH[C(O)SR"]$_2$, —CH[C(S)SR"]$_2$, —CH$_2$OR", or —CH$_2$SR"; and R' and R", independently of each another, represents hydrogen, alkyl, cycloalkyl, alkenyl, alkynyl, or alkoxy.

In a more preferred embodiment, the triaryl methane derivative for use according to the invention is represented by the general Formula VI wherein;

the partially or completely saturated mono- or polycyclic aryl group is elected from the group consisting phenyl, biphenyl, naphthyl, or cyclopenta-2,4-diene-1-ylidene; and the mono- or poly-heterocyclic group is A 5- and 6 membered heterocyclic monocyclic group selected from the group consisting of furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, piperidyl, pyrazinyl, pyrazolyl, pyridazinyl, pyridyl, pyrimidinyl, pyrrolidinyl, pyrrolyl, thiadiazolyl, thiazolyl, thienyl, and butyrolactonyl, in particular γ-butyrolactonyl.

In a seventh preferred embodiment the triaryl methane derivative for use according to the invention is represented by the general Formula VII

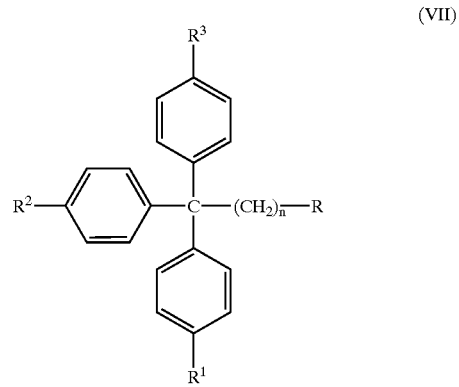

(VII)

and a pharmaceutically acceptable salt or an oxide or a hydrate thereof, wherein, n is 0, 1, 2, 3, 4, 5, or 6;

R represents hydrogen, halogen, trihalogenmethyl, alkyl, cycloalkyl, alkenyl, alkynyl, amino, nitro or cyano, or a group of the formula —OR', —SR', —R"OR', —R"SR', —C(O)R', —C(S)R', —C(O)OR', —C(S)OR', —C(O)SR', —C(S)SR', —C(O)NR"(OR'), —C(S)NR"(OR'), —C(O)NR"(SR'), —C(S)NR"(SR'), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, —CH$_2$OR', or —CH$_2$SR'; or a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR', or —SR';

$R^1$, $R^2$ and $R^3$, independently of each another, represents hydrogen, halogen, trihalogenmethyl, alkyl, cycloalkyl, alkenyl, alkynyl, amino, nitro or cyano, or a group of the formula —OR", —SR", —R'OR", —R'SR", —C(O)R", —C(S)R", —C(O)OR", —C(S)OR", —C(O)SR", —C(S)SR", —C(O)NR'(OR"), —C(S)NR'(OR"), —C(O)NR'(SR"), —C(S)NR'(SR"), —CH(CN)$_2$, —C(O)NR"$_2$, —C(S)NR"$_2$, —CH[C(O)R"]$_2$, —CH[C(S)R"]$_2$, —CH[C(O)OR"]$_2$, —CH[C(S)OR"]$_2$, —CH[C(O)SR"]$_2$, —CH[C(S)SR"]$_2$, —CH$_2$OR", or —CH$_2$SR"; and R' and R", independently of each another, represents hydrogen, alkyl, cycloalkyl, alkenyl, alkynyl, or alkoxy.

In a more preferred embodiment, the triaryl methane derivative for use according to the invention is represented by the general Formula VII wherein;

the partially or completely saturated mono- or polycyclic aryl group is selected from the group consisting phenyl, biphenyl, naphthyl, or cyclopenta-2,4-diene-1-ylidene; and the mono- or poly-heterocyclic group is A 5- and 6 membered heterocyclic monocyclic group selected from the group consisting of furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, piperidyl, pyrazinyl, pyrazolyl, pyridazinyl, pyridyl, pyrimidinyl, pyrrolidinyl, pyrrolyl, thiadiazolyl, thiazolyl, thienyl, and butyrolactonyl, in particular γ-butyrolactonyl.

In an eight preferred embodiment the triaryl methane derivative for use according to the invention is represented by the general Formula VIII

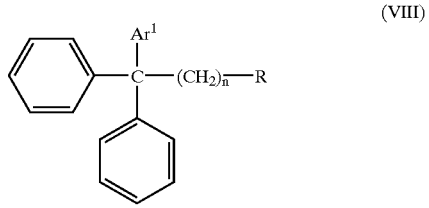

(VIII)

and a pharmaceutically acceptable salt or an oxide or a hydrate thereof, wherein, n is 0, 1, 2, 3, 4, 5, or 6;

$Ar^1$ represents a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR", —SR", —R'OR", —R'SR", —C(O)R", —C(S)R", —C(O)OR", —C(S)OR", —C(O)SR", —C(S)SR", —C(O)NR'(OR"), —C(S)NR'(OR"), —C(O)NR'(SR"), —C(S)NR'(SR"), —CH(CN)$_2$, —C(O)NR"$_2$, —C(S)NR"$_2$, —CH[C(O)R"]$_2$, —CH[C(S)R"]$_2$,—CH[C(O)OR"]$_2$,—CH[C(S)OR"]$_2$, —CH[C(O)SR"]$_2$, —CH[C(S)SR"]$_2$, —CH$_2$OR", or —CH$_2$SR";

R represents hydrogen, halogen, trihalogenmethyl, alkyl, cycloalkyl, alkenyl, alkynyl, amino, nitro or cyano, or a group of the formula —OR', —SR', —R"OR', —R"SR', —C(O)R', —C(S)R', —C(O)OR', —C(S)OR', —C(O)SR', —C(S)SR', —C(O)NR"(OR'), —C(S)NR"(OR'), —C(O)NR"(SR'), —C(S)NR"(SR'), —CH(CN)$_2$, —C(O)NR'$_2$, —C(S)NR'$_2$, —CH[C(O)R']$_2$, —CH[C(S)R']$_2$, —CH[C(O)OR']$_2$, —CH[C(S)OR']$_2$, —CH[C(O)SR']$_2$, —CH[C(S)SR']$_2$, —CH$_2$OR', or —CH$_2$SR'; or a partially or completely saturated mono- or polycyclic aryl group, or a mono- or poly-heterocyclic group, which mono- or polycyclic groups may optionally be substituted one or more times with substituents selected from the group consisting of hydrogen, halogen, trihalogenmethyl, alkyl, cycloalkyl, alkenyl, alkynyl, amino, nitro or cyano, or a group of the formula —OR', or —SR';

R' and R", independently of each another, represents hydrogen, alkyl, cycloalkyl, alkenyl, alkynyl, or alkoxy.

In a more preferred embodiment, the triaryl methane derivative for use according to the invention is represented by the general Formula VIII wherein;

the partially or completely saturated mono- or polycyclic aryl group is selected from the group consisting phenyl, biphenyl, naphthyl, or cyclopenta-2,4-diene-1-ylidene; and the mono- or poly-heterocyclic group is A 5- and 6 membered heterocyclic monocyclic group selected from the group consisting of furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, piperidyl, pyrazinyl, pyrazolyl, pyridazinyl, pyridyl, pyrimidinyl, pyrrolidinyl, pyrrolyl, thiadiazolyl, thiazolyl, thienyl, and butyrolactonyl, in particular γ-butyrolactonyl.

Definition of Substituents

In the context of this invention halogen represents a fluorine, a chlorine, a bromine or a iodine atom. Thus, a trihalogenmethyl group represents e.g. a trifluoromethyl group and a trichloromethyl group.

In the context of this invention an alkyl group designates a univalent saturated, straight or branched hydrocarbon chain. The hydrocarbon chain preferably contain of from one to eighteen carbon atoms ($C_{1-18}$-alkyl), more preferred a lower alkyl of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a most preferred embodiment alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, and cyclohexyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1,2- or 2,3-propenyl; or 1,2-, 2,3-, or 3,4-butenyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl, 1,2- or 2,3-propynyl, 1,2-, 2,3- or 3,4-butynyl.

In the context of this invention an alkoxy group designates an "alkyl-O—" group, wherein alkyl is as defined above.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

In the context of this invention a mono- or polycyclic aryl group designates a monocyclic or polycyclic aromatic hydrocarbon group. Examples of preferred aryl groups of the invention are phenyl, biphenyl, naphthyl and anthracenyl.

In the context of this invention a mono- or polyheterocyclic group is a mono- or polycyclic aromatic group, which holds one or more heteroatoms in its ring structure. Preferred heterocyclic monocyclic groups of the invention are 5- and 6 membered heterocyclic monocyclic groups. Examples of preferred heterocyclic monocyclic groups of the invention include furanyl, imidazolyl, isoimidazolyl, 2-isoimidazolyl, isothiazolyl, isoxazolyl, 1,2,3-oxadiazolyl, 1,2,4-oxadiazolyl, 1,2,5-oxadiazolyl, 1,3,4-oxadiazolyl, oxazolyl, pyrazinyl, pyrazolyl, pyridazinyl, pyridyl, pyrimidinyl, pyrrolyl, thiadiazolyl, thiazolyl, and thienyl. Examples of preferred heterocyclic polycyclic groups of the invention include benzimidazolyl, indolyl, isoquinolyl and quinolyl.

The chemical compounds for use according to the invention have been described and may be prepared by methods known in the art.

Pharmaceutically Acceptable Salts

The chemical compound for use according to the invention may be provided in any form suitable for the intended administration. Suitable forms include pharmaceutically (i.e. physiologically) acceptable salts, or pre- or prodrug forms of the chemical compound for use according to the invention.

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound for use according to the invention and its pharmaceutically acceptable acid addition salt.

Metal salts of a chemical compound for use according to the invention includes alkali metal salts, such as the sodium salt, of a chemical compound for use according to the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The chemical compound for use according to the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Moreover, some of the chemical compounds for use according to the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Biological Activity

As described above, the $IK_{Ca}$ inhibitory compounds for use according to the invention are particularly useful as immune modulating agents, i.e. agents capable of regulating the immune system. More particularly, the $IK_{Ca}$ inhibitory compounds of the present invention may be used for reducing or inhibiting undesired immune-regulatory actions.

In a preferred embodiment, the invention relates to the use of an $IK_{Ca}$ inhibitory compound for the treatment or alleviation of a diseases, disorders or condition related to immune dysfunction, or in order to obtain immune suppression in an individual in need herefore.

In a more preferred embodiment, the invention relates to the use of an $IK_{Ca}$ inhibitory compound of the invention in a combination therapy with known immune-suppressants for the treatment or alleviation of a diseases, disorders or condition related to immune dysfunction, or for obtaining immune suppression. Preferred immune-suppressants to combine with the compounds of the invention include Amphotericin, Busulphan, Co-trimoxazole, Chlorambucil, colony stimulating factors, corticosteroids, Cyclophosphamide, Fluconazole, folinic acid, Ganciclovir, antilymphocyte immunoglobulins, normal immunoglobulins, Methotrexate, Methylprednisolone, Octreotide, Oxpentifylline, Tacrolimus (FK506), Thalidomide, Zolimomab aritox, and the calcineurin inhibitors (protein phosphatase 2B inhibitors), in particular Cyclosporin.

Conditions which may benefit from this treatment include, but are not limited to diseases, disorders or conditions such as auto-immune diseases, e.g. Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Chron's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, auto-immune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminate, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Lesihmania, and immune-suppressed disease states such as viral infections following allograft transplantations, graft vs. Host syndrome, transplant rejection, or AIDS, cancer, chronic active hepatitis diabetes, toxic chock syndrome, food poisoning, and transplant rejection.

Accordingly, in further embodiments, the invention relates to a chemical compound having $IK_{Ca}$ inhibitory activity for use as a medicament.

More specifically the invention relates to the use of a chemical compound having selective $IK_{Ca}$ inhibitory activity for use in the manufacture of a medicament for the treatment of treatment of diseases related to immune dysfunction. In a preferred embodiment the medicament is an immune system suppressing medicament (an immune-suppressivum).

Pharmaceutical Compositions

In yet another aspect the invention relates to pharmaceutical compositions for use in the treatment or alleviation of diseases, disorders or conditions related to immune dysfunction, which pharmaceutical composition comprises a therapeutically effective amount of a chemical compound having $IK_{Ca}$ inhibitory activity, as identified by the method of the invention.

While a chemical compound for use according to the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound for use according to the invention or a pharmaceutically acceptable salt or derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

The pharmaceutical composition of the invention may be administered by any convenient route which suite the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 $\mu$g/kg i.v. and 1 $\mu$g/kg p.o. The upper limit of the dosage range is presently considered to be about 10 mg/kg i.v. and 100 mg/kg p.o. Preferred ranges are from about 0.1 $\mu$g/kg to about 10 mg/kg/day i.v., and from about 1 $\mu$g/kg to about 100 mg/kg/day p.o.

Methods of Therapy

Viewed from another aspect, the invention provides a method for treatment, prevention or alleviation of a disease or a disorder or a condition of a living animal body, including a human, which disease, disorder or condition is responsive to $IK_{Ca}$ inhibitory compounds.

Therefore, in a preferred embodiment, the invention provides a method of treatment or alleviation of diseases, disorders or conditions relating to immune dysfunction in a living body, said method comprising administering to said living body an effective amount of a chemical compound having $IK_{Ca}$ inhibitory activity.

In a more preferred embodiment, the disease, disorder or condition relating to immune dysfunction is an auto-immune disease, e.g. Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Chron's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, auto-immune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminate, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Lesihmania, and immune-suppressed disease states such as viral infections following allograft transplantations, graft vs. Host syndrome, transplant rejection, or AIDS, cancer, chronic active hepatitis diabetes, toxic chock syndrome, food poisoning, or transplant rejection.

In another preferred embodiment, the method of the invention comprises simultaneous administration of the chemical compound having selective $IK_{Ca}$ inhibitory activity and a pharmaceutically effective amount of a conventional immune suppressing agent.

In a more preferred embodiment the immune-suppressing agent is Amphotericin, Busulphan, Co-trimoxazole, Chlorambucil, colony stimulating factors, corticosteroids, Cyclophosphamide, Fluconazole, folinic acid, Ganciclovir, antilymphocyte immunoglobulins, normal immunoglobulins, Methotrexate, Methylprednisolone, Octreotide, Oxpentifylline, Tacrolimus (FK506), Thalidomide, Zolimomab aritox, or the calcineurin inhibitors (protein phosphatase 2B inhibitors), in particular Cyclosporin.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

BRIEF DESCRIPTION OF THE DRAWINGS

The present invention is further illustrated by reference to the accompanying drawing, in which.

EXAMPLES

Figure 1:
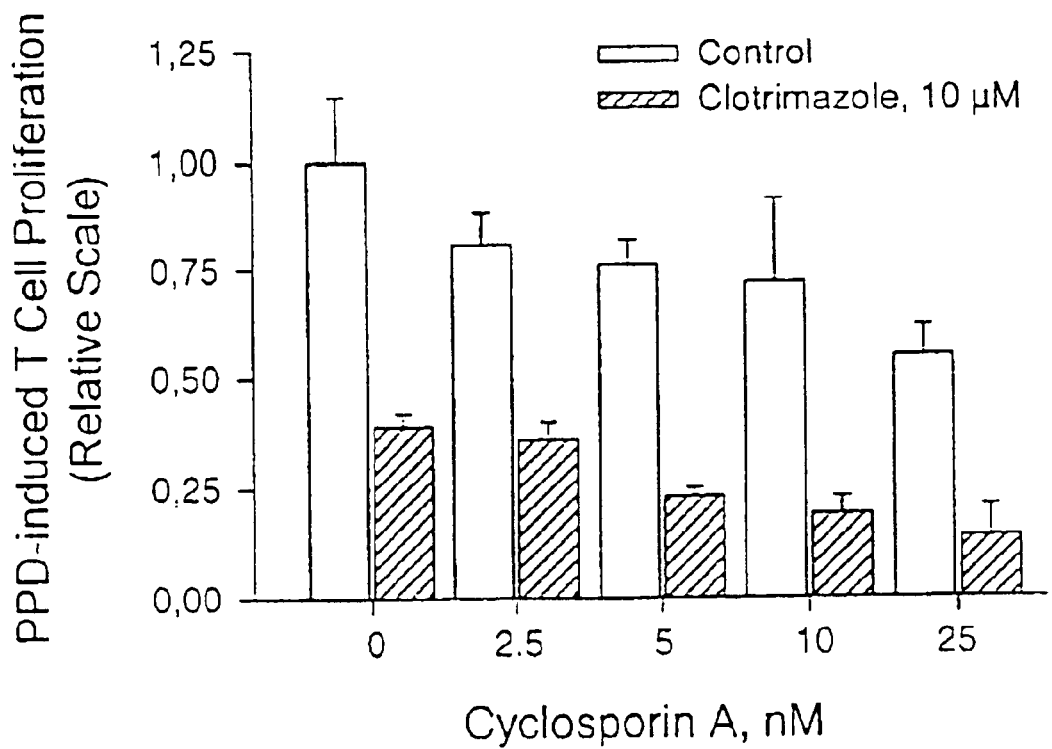
FIG. 1 shows the effect of a compound of the invention (Clotrimazole) on Cyclosporin A mediated inhibition of T cell proliferation (PPD-induced T cell proliferation) on a relative scale of from 0,00 to 1,25, carried out as described in Example 2 [with and without (Control) Clotrimazole, 10 $\mu$M; Combined with Cyclosporin A, in concentrations of 0, 2.5, 5, 10 and 25 nM, respectively].

The invention is further illustrated with reference to the following examples which are not intended to be in any way limiting to the scope of the invention as claimed.

Example 1
Inhibition of T Cell Proliferation

The chemical compounds used according to the invention prevent immunological proliferation by selective inhibition of the $Ca^{2+}$-activated K-channels in T- and B-lymphocytes. This effect may be verified using various proliferation assays. In this experiment the proliferative assay described by Ødum et al. [Ødum N, Kanner S B, Ledbetter J A, & Svejgaard A; *J. Immunol.* 1993 150 (12) 5289–5298] was used.

The chemical compounds representative for the invention tested in this experiment are (4-chlorophenyl-diphenyl)-carbinol (A); ethyl-2-phenyl-2-(1-piperidyl)-phenylacetate (B); and 1,1,1-triphenylacetone (C); all compounds commercially available from Sigma-Aldrich, Denmark.

Assays were performed in culture medium (RPMI 1640; available from Gibco, Grand Island, N.Y.) supplemented with 10% pooled human serum, 2 mM L-glutamine, 100 µg/ml penicillin, and 100 µg/ml streptomycin (available from Novo Nordisk, Copenhagen, Denmark) in 96-well round bottom tissue culture plates (available from Nunc, Roskilde, Denmark) with a final volume of 200 µl.

T cells were pre-incubated for three hours with the test compounds before addition of antigen (PPD; Purified protein derivative, available from Statens Serum Institut, Denmark; 100 µg/ml). T cells were cultured at 5×10⁴ cells/well for 144 hours. Twelve hours before harvest, [³H]thymidine (1×Ci/well) was added. The cells were harvested onto glass fibre filters, and the [³H]thymidine incorporation was measured in a scintillation counter. The results were expressed as mean counts per minute (cpm) from triplicate cultures.

The results are presented in Table 1, below.

TABLE 1

Inhibition of T Cell Proliferation

| Test Compound | Medium Solvent | T Cell Proliferation (cpm × 10⁻³) Antigen, PPD | | | |
|---|---|---|---|---|---|
| | | Solvent | 2.5 µM | 10 µM | 25 µM |
| A | 0.2 | 26.1 | 21.5 | 19.8 | 18.1 |
| B | 0.2 | 26.1 | 22.5 | 20 | 19 |
| C | 0.2 | 26.1 | 25.5 | 18 | 19 |

These results show that the number of T cells decreases in the presence of increasing concentrations of the chemical compound for use according to the invention, and support the fact that the chemical compounds for use according to the invention inhibit the antigen induced T cell proliferation and thus are useful for the reduction or inhibition of undesired immune-regulatory actions.

Example 2
Combination Treatment

In this example, the effect of a compound of this invention (Clotrimazole) on Cyclosporin A mediated inhibition of T cell proliferation is determined.

T cells were stimulated with antigen in the presence of Cyclosporin A, or Cyclosporin A and Clotrimazole, respectively.

The proliferation assay described in Example 1, was used.

Cells were incubated for 5 days in culture medium with PPD in the presence of Cyclosporin A, or Cyclosporin A and Clotrimazole, respectively. Clotrimazole (10 µM) was added 30 minutes prior to the addition of antigen. [³H]thymidine (1 mM Ci) incorporation was then measured in triplicate wells. The bars shown in FIG. 1 represent 3 independent experiments ±S.E. (p≤0.05 vs. control). Eleven other experiments using *Candida albicans* antigen, tetanus toxin, Con A or PHA as the antigen/mitogen challenge gave similar results.

T cell proliferation was assayed 6 days after stimulation using 3H-thymidine incorporation. The Cyclosporin A mediated inhibition of T cell proliferation is shifted leftwards by 10 µM Clotrimazole, from a 50% inhibition of proliferation at approximately 25 nM Cyclosporin A to half-maximal inhibition at 2.5 nM Cyclosporin A.

This suggests that the antigen-induced T cell proliferation is highly sensitive to both IK channel block and inhibition of calcineurin, and data indicate that the IK channel is highly important for normal T cell proliferation and suggest that IK channels are attractive targets for immune suppression.

What is claimed:

1. A method for inhibiting T cell proliferation, said method comprising administering a therapeutically effective amount of a chemical compound having selective $IK_{Ca}$ modulatory activity to said mammal, wherein the chemical compound is a triaryl methane derivative represented by Formula VIII

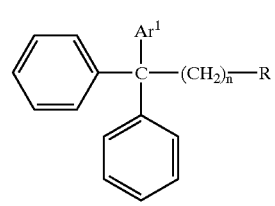

(VIII)

or a pharmaceutically acceptable salt or an oxide or a hydrate thereof, wherein n is 0;

$Ar^1$ represents a phenyl, furanyl, imidazolyl, oxazolyl, piperidyl, pyridyl, pyrimidinyl, pyrrolyl, thiazolyl or thienyl group, which group may optionally be substituted one or more times with substituents selected from the group consisting of halogen, trihalogenmethyl, alkyl, cycloalkyl, amino, nitro and cyano; and R represents —OR', —C(O)R', —C(O)OR', —C(O)NR'₂ or —CH₂OR', wherein R' represents hydrogen, alkyl or cycloalkyl.

2. The method according to claim 1, wherein the compound is (4-chlorophenyl-diphenyl)-carbinol; Ethyl 2-phenyl-2-(1-piperidyl)-phenylacetate; or 1,1,1-triphenylacetone; or a pharmaceutically acceptable salt or an oxide or a hydrate thereof.

3. The method according to claim 1, said method further comprising administering a pharmaceutically effective amount of a conventional immune suppressing agent to said mammal.

4. The method according to claim 3, wherein the immune-suppressing agent is Amphotericin, Busulphan, Co-trimoxazole, Chlorambucil, colony stimulating factors, corticosteroids, Cyclophosphamide, Fluconazole, folinic acid, Ganciclovir, antilymphocyte immunoglobulins, normal immunoglobulins, Methotrexate, Methylprednisolone, Octreotide, Oxpentifylline, Tacrolimus (FK506), Thalidomide, Zolimomab aritox, or the calcineurin inhibitors (protein phosphatase 2B inhibitors).

5. The method according to claim 3, wherein the conventional immune-suppressing agent is Cyclosporin.

6. The method according to claim 2, wherein said compound is (4-chlorophenyl-diphenyl)-carbinol.

* * * * *